ic011517272B2

United States Patent
Unklesbay et al.

(10) Patent No.: US 11,517,272 B2
(45) Date of Patent: Dec. 6, 2022

(54) SIMULATED ORTHODONTIC TREATMENT VIA AUGMENTED VISUALIZATION IN REAL-TIME

(71) Applicant: 3M INNOVATIVE PROPERTIES COMPANY, St. Paul, MN (US)

(72) Inventors: Amy Unklesbay, Stillwater, MN (US); Cody J. Olson, Ham Lake, MN (US); Richard E. Raby, Lino Lakes, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 17/051,908

(22) PCT Filed: May 2, 2019

(86) PCT No.: PCT/IB2019/053599
§ 371 (c)(1),
(2) Date: Oct. 30, 2020

(87) PCT Pub. No.: WO2019/215550
PCT Pub. Date: Nov. 14, 2019

(65) Prior Publication Data
US 2021/0045701 A1 Feb. 18, 2021

Related U.S. Application Data

(60) Provisional application No. 62/809,806, filed on Feb. 25, 2019, provisional application No. 62/669,628, filed on May 10, 2018.

(51) Int. Cl.
*A61B 6/14* (2006.01)
*G06F 3/048* (2013.01)
(Continued)

(52) U.S. Cl.
CPC .............. *A61B 6/14* (2013.01); *A61B 6/4085* (2013.01); *A61B 6/466* (2013.01); *G06F 3/011* (2013.01); *G06F 3/048* (2013.01)

(58) Field of Classification Search
CPC ......... A61B 6/14; A61B 6/4085; A61B 6/466; A61B 5/0077; G06F 3/011; G06F 3/048; A61C 7/14; A61C 7/002; A61C 7/12
See application file for complete search history.

(56) References Cited

U.S. PATENT DOCUMENTS

2002/0010568 A1   1/2002  Rubbert
2004/0197727 A1*  10/2004 Sachdeva ........... A61C 13/0004
                                                          433/24
(Continued)

FOREIGN PATENT DOCUMENTS

JP        2013128694       7/2013
WO     WO 2015/170162     11/2015
(Continued)

OTHER PUBLICATIONS

"Deep Learning," Wikipedia, [retrieved from the internet on Dec. 29, 2020], URL <https://en.wikipedia.org/wiki/Deep_learning>, 2020, pp. 1-31.
(Continued)

*Primary Examiner* — Jitesh Patel
(74) *Attorney, Agent, or Firm* — Sriram Srinivasan; Lance L. Vietzke

(57) ABSTRACT

A system and method for simulating orthodontic treatment using augmented reality. An electronic image of a user's face is received from a digital camera, and a region of interest in the image is identified where the region includes the user's teeth. Virtual orthodontic appliances are placed on the user's teeth in the image, and the user's image with the virtual orthodontic appliances is displayed on an electronic display device. The method occurs in real-time to provide the user
(Continued)

with the augmented image simulating treatment when or shortly after the image of the user is received. The system and method can display a 3D representation of the user's face augmented with the virtual appliances. The user's augmented image or 3D representation can also be supplemented for display with an image or model of the user's facial anatomy such as an x-ray or a cone beam computed tomography image.

16 Claims, 6 Drawing Sheets

(51) Int. Cl.
*A61B 6/00* (2006.01)
*G06F 3/01* (2006.01)

(56) References Cited

U.S. PATENT DOCUMENTS

| | | | |
|---|---|---|---|
| 2007/0218418 A1 | 9/2007 | Raby | |
| 2008/0096152 A1 | 4/2008 | Gheang | |
| 2010/0106465 A1* | 4/2010 | Sporbert | A61C 7/00 703/1 |
| 2010/0234724 A1* | 9/2010 | Jacobsen | A61B 90/37 600/424 |
| 2014/0122027 A1* | 5/2014 | Andreiko | A61B 1/24 703/1 |
| 2014/0146142 A1 | 5/2014 | Duret et al. | |
| 2015/0169938 A1* | 6/2015 | Yao | G06K 9/00261 382/103 |
| 2015/0347822 A1* | 12/2015 | Zhou | G06K 9/00248 382/118 |
| 2016/0228214 A1 | 8/2016 | Sachdeva et al. | |
| 2017/0007368 A1 | 1/2017 | Boronkay | |
| 2018/0104022 A1 | 4/2018 | Cheang | |
| 2018/0174367 A1* | 6/2018 | Marom | G06F 3/011 |
| 2019/0117337 A1* | 4/2019 | Tsai | A61C 7/002 |
| 2020/0320685 A1* | 10/2020 | Anssari Moin | G06V 10/454 |

FOREIGN PATENT DOCUMENTS

| | | |
|---|---|---|
| WO | WO 2016-003255 | 1/2016 |
| WO | WO 2018/022940 | 2/2018 |

OTHER PUBLICATIONS

"Noise Reduction," Wikipedia, [retrieved from the internet on Dec. 29, 2020], URL <https://en.wikipedia.org/wiki/Noise_reduction>, 2020, pp. 1-11.
"Perspective-n-Point," Wikipedia, [retrieved from the internet on Dec. 29, 2020], URL <https://en.wikipedia.org/wiki/Perspective-n-Point>, 2020, pp. 1-5.
"Principal Component Analysis," Wikipedia, [retrieved from the internet on Dec. 29, 2020], URL <http://en.wikipedia.org/wiki/Principal_component_analysis>, 2020, pp. 1-27.
"Structure from Motion," Wikipedia, [retrieved from the internet on Dec. 29, 2020], URL, <https://en.wikipedia.org/wiki/Structure_from_motion>, 2020, pp. 1-8.
"Support Vector Machine," Wikipedia, [retrieved from the internet on Dec. 29, 2020], URL <https://en.wikipedia.org/wiki/Support_vector_machine>, 2020, pp. 1-18.
Kaehler, "Chapter 10: Filters and Convolution," Learning OpenCV 3, Computer Vision in C++ with the OpenCV Library, 2016, pp. 259-261.
Kaehler, "Chapter 10: Filters and Convolution," Learning OpenCV 3, Computer Vision in C++ with the OpenCV Library, 2016, pp. 276-290.
Kaehler, "Chapter 12: Image Analysis," Learning OpenCV 3, Computer Vision in C++ with the OpenCV Library, 2016, pp. 368-370.
Kaehler, "Chapter 14: Contours," Learning OpenCV 3, Computer Vision in C++ with the OpenCV Library, 2016, pp. 407-441.
Nixon, "Chapter 4: Low-level Feature Extraction (Including Edge Detection)," Feature Extraction & Image Processing for Computer Vision, Third Edition, 2012, pp. 137-173.
Nixon, "Chapter 8: Texture Description, Segmentation, and Classification," Feature Extraction & Image Processing for Computer Vision, Third Edition, 2012, pp. 411-417.
Prince, "Chapter 11: Models for Chains and Trees," Computer Vision: Models, Learning, and Inference, 2012, pp. 270-271.
Prince, "Chapter 11: Models for Chains and Trees," Computer Vision: Models, Learning, and Inference, 2012, p. 272.
Prince, "Chapter 12: Models for Grids," Computer Vision: Models, Learning, and Inference, 2012, pp. 279-281.
Viola, "Robust Real-Time Face Detection," International Journal of Computer Vision, 2004, vol. 57, No. 02, pp. 137-154.
International Search Report for PCT International Application No. PCT/IB2019/053599, dated Sep. 5, 2019, 7 pages.
Kehler Jacob: "Nerdy Glasses and Braces Snapchat lens, On The Line Social Media", Aug. 1, 2016 (2016-08-01), XP055874300, Retrieved from the Internet: URL: https://web.archive.org/web/20160801141348/http://otlsm.com:80/nerdy-glasses-and-braces-snapchat-lens [retrieved on 2021-12-17], 2 pp.

* cited by examiner

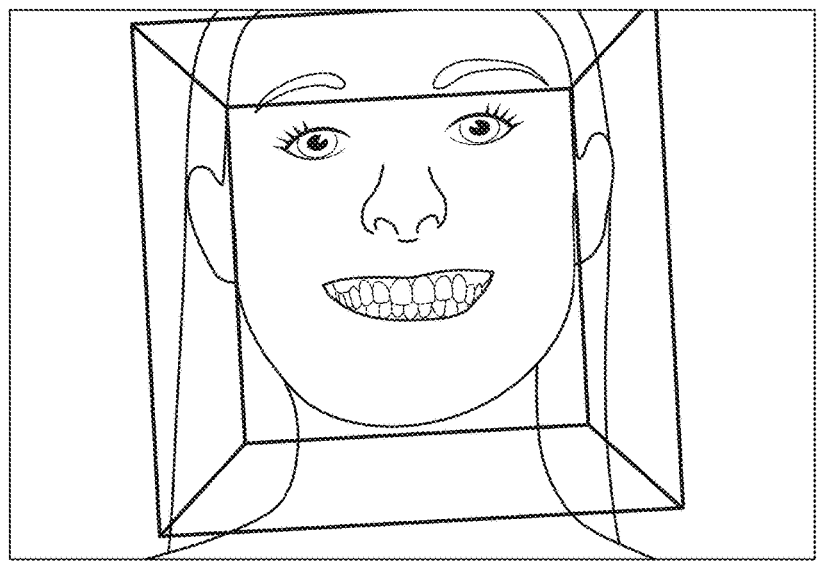
*FIG. 5*
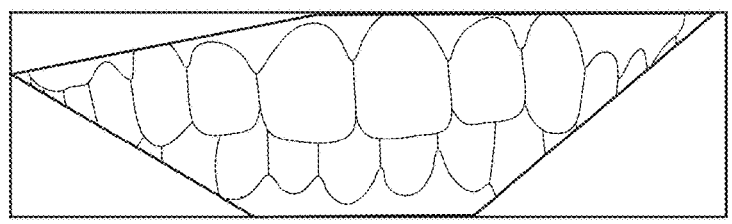
*FIG. 6*
*FIG. 7A*   *FIG. 7B*   *FIG. 7C*
*FIG. 8A*   *FIG. 8B*   *FIG. 8C*

*FIG. 9A*  *FIG. 9B*
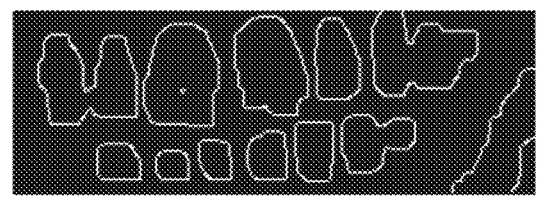
*FIG. 10*
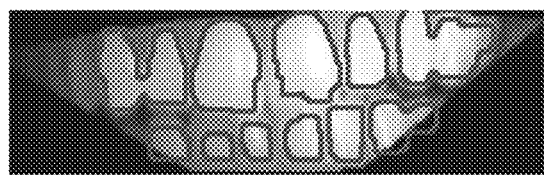  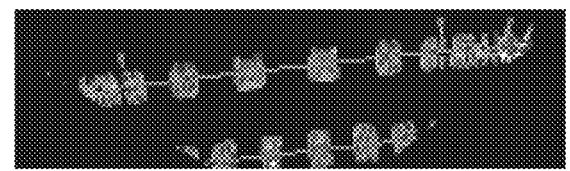
*FIG. 11*  *FIG. 12*
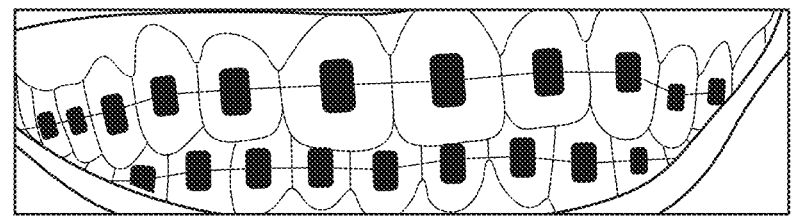
*FIG. 13*

SIMULATED ORTHODONTIC TREATMENT VIA AUGMENTED VISUALIZATION IN REAL-TIME

CROSS REFERENCE TO RELATED APPLICATIONS

This application is a national stage filing under 35 U.S.C. 371 of PCT/IB2019/053599 filed May 2, 2019, which claims the benefit of U.S. Provisional Application Nos. 62/669,628, filed May 10, 2018, and 62/809,806, filed Feb. 25, 2019, the disclosures of which are incorporated by reference in their entireties herein.

BACKGROUND

The use of augmented reality face filters, such as the SNAPCHAT or INSTAGRAM products, are becoming increasingly popular. However, these filters are mainly used in popular culture today for only entertainment purposes, such as to visually apply renditions of hair, make-up, eyeglasses, facial hair, and hats in real-time to the face or head of the human subject in a video augmentation. A need exists to extend this technology for use in medical or dental applications.

SUMMARY

A method for simulating orthodontic treatment of an embodiment of the invention includes receiving an electronic image of a user's face and identifying a region of interest in the image including the user's teeth. Virtual orthodontic appliances are placed on the user's teeth in the image or detected appliances are removed, and the user's image with the virtual orthodontic appliances or without the detected appliances is displayed on an electronic display device. The method occurs in real-time to provide the user with the augmented image simulating treatment when or shortly after the image of the user is received.

A system for simulating orthodontic treatment of an embodiment of the invention includes a camera providing electronic digital images or video, an electronic display device, and a processor. The processor is configured to receive an electronic image of a user's face from the camera, identify a region of interest in the image including the user's teeth, place virtual orthodontic appliances on the user's teeth in the image or remove detected appliances, and display on the electronic display device the user's image with the virtual orthodontic appliances or without the detected appliances. The processor operates in real-time to provide the user with the augmented image simulating treatment when or shortly after the image of the user is received from the camera.

Another method for simulating orthodontic treatment of an embodiment of the invention includes receiving an electronic image of a user's face and retrieving an electronic image or model of a user's facial anatomy. The method also includes identifying a region of interest in the image where the region of interest includes the user's teeth and placing virtual orthodontic appliances on the user's teeth in the image. The user's image with the virtual orthodontic appliances and with the image or model of the user's facial anatomy is displayed on electronic display device. The method occurs in real-time to provide the user with the augmented image simulating treatment when or shortly after the image of the user is received.

Another system for simulating orthodontic treatment of an embodiment of the invention includes a camera providing electronic digital images or video, an electronic display device, and a processor. The processor is configured to receive an electronic image of a user's face, retrieve an electronic image or model of a user's facial anatomy, identify a region of interest in the image where the region of interest includes the user's teeth, place virtual orthodontic appliances on the user's teeth in the image, and display on an electronic display device the user's image with the virtual orthodontic appliances and with the image or model of the user's facial anatomy. The processor operates in real-time to provide the user with the augmented image simulating treatment when or shortly after the image of the user is received from the camera.

BRIEF DESCRIPTION OF THE DRAWINGS

The accompanying drawings are incorporated in and constitute a part of this specification and, together with the description, explain the advantages and principles of the invention. In the drawings.

FIG. 5 is a representation of an image illustrating face pose estimation;

FIG. 6 illustrates a cropped region of interest;

FIGS. 7A-7C illustrate adaptive thresholding applied to an inverted channel;

FIGS. 8A-8C illustrate adaptive thresholding applied to a luminance channel;

FIGS. 9A and 9B illustrate opening and closing of a region of interest;

FIG. 10 illustrates detected edges;

FIG. 11 illustrates closed contours from detected edges;

FIG. 12 illustrates virtual rendering of treatment;

FIG. 13 illustrates augmentation of treatment;

DETAILED DESCRIPTION

Figure 1:
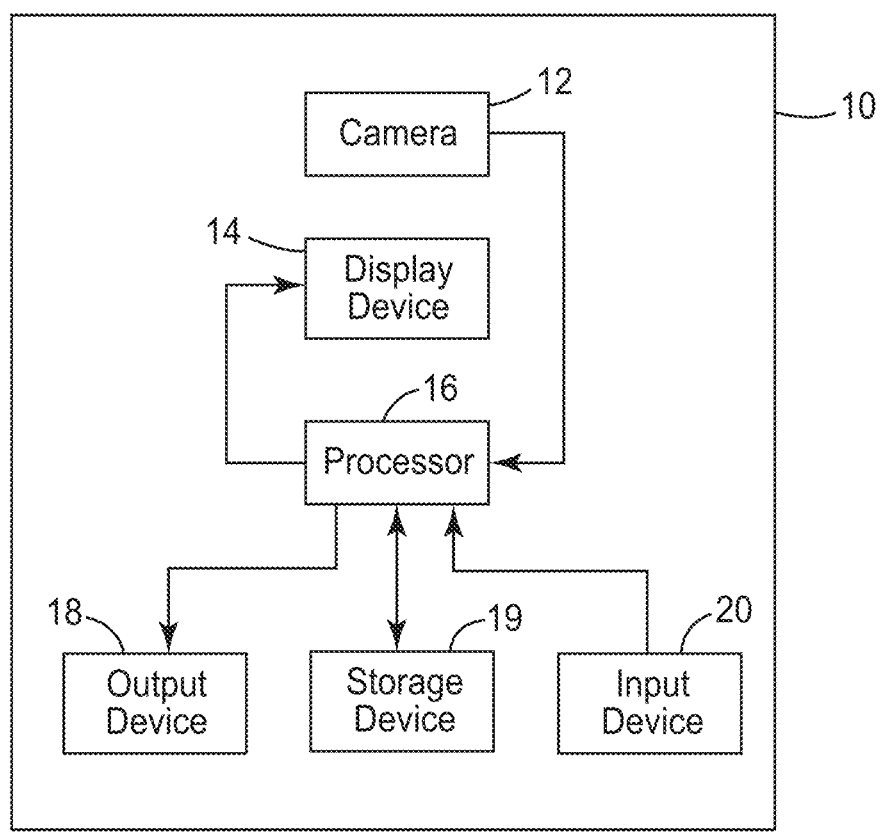
FIG. 1 is a diagram of a system for simulating orthodontic treatment.

Embodiments of this invention include the use of computer vision and augmented reality technology to superimpose a computer-generated image on a user's view of the real world to provide a view of one, or combination, of the following:

1. The addition or subtraction of orthodontic appliance(s), such as lingual brackets, labial brackets, aligners, class correction devices, or retention devices.

2. The addition, subtraction, or modification of dental restoration(s), such as crowns, bridges, inlays, onlays, veneers, dentures, or gingiva.

3. The addition, subtraction, or modification of natural tooth anatomy, such as by using tooth whitening agents, reducing or building-up cusp tips or incisal edges, or predicting the appearance of teeth after eruption in children (possibly including ectopic eruptions).

4. The modification of craniofacial structures via oral or maxillofacial surgery, including dentoalveolar surgery, dental and maxillofacial implants, cosmetic surgery, and orthognathic surgery.

5. The addition, subtraction, or modification of maxillofacial, ocular, or craniofacial prosthesis.

6. The result of orthodontic and/or restorative treatment—to include the planned positions and shapes of dental anatomical structures, i.e. teeth and gingiva.

7. The predicted result of not undergoing orthodontic and/or restorative treatment, possibly showing deleterious consequences, such as malocclusion, tooth wear, gingival recession, gum disease, bone loss, tooth decay, or tooth loss.

8. The modification of soft tissues of the face, such as by botulinum toxin injections or more invasive cosmetic and plastic surgeries, such as rhinoplasty, chin enhancement, cheek enhancement, facelift, eyelid lift, neck lift, brow lift, cleft palate repair, burn repair, and scar revision.

9. An overlay, of variable opacity, of staged treatment—to compare scheduled versus actual progress of treatment.

This technology can be used both as a tool for treatment planning by a medical/dental professional and as a tool for case presentation to a patient. Other intended uses include exploration of treatment options by a patient wanting to visualize their facial appearance during or after treatment, possibly switching or transitioning between before and after appearances for comparison. In some cases, a patient may be able to entertain treatment scenarios without first visiting a medical or dental practitioner, using only superficial imagery data. In other cases, the augmentation may require additional data, such as X-ray or cone beam computed tomography (CBCT) scan data, bite registration data, three-dimensional (3D) oral scan data, virtual articulation data, or calibrated measurements in order to generate a treatment plan that provides a more accurate rendition of the patient after treatment. As such, additional time and effort may be needed to clean-up and integrate datasets, explore treatment options, perform measurements and analyses, and plan treatment steps before a credible rendition of treatment outcome can be shown to the patient. In some cases, two or more treatment scenarios may be generated and presented to the patient, thereby giving the patient a somewhat realistic view of treatment outcome. This can serve to help the patient (or doctor) in deciding on a course of action. In some cases, the cost of treatment may be weighed against the quality of outcome. For example, the patient may forego an expensive treatment due to marginal gains in appearance over a less expensive treatment. Similar rules may be applied to the duration of treatment, where time is treated like a cost.

System and Method

FIG. 1 is a diagram of a system 10 for simulating orthodontic treatment. System 10 includes a processor 16 electronically coupled with a camera 12, a display device 14, an output device 18, a storage device 19, and an input device 20. Camera 12 can be implemented with, for example, a digital image sensor providing electronic digital images or video. Display device 14 can be implemented with any electronic display, for example a Cathode Ray Tube (CRT), a liquid crystal display (LCD), light emitting diode (LED) display, or organic light emitting diode (OLED) display. Output device 18 can be implemented with any device for outputting information, for example a speaker, an LED indicator, or an auxiliary LCD display module. Input device 20 can be implemented with any device for entering information or commands, for example a keyboard, microphone, cursor-control device, or touch screen. Storage device 19 can be implemented with any electronic device for storing information such as a hard drive, solid state drive, or flash drive. Storage device 19 can optionally be located external to system 10 and accessed via a network connection. System 10 can be implemented with, for example, a desktop, notebook, or tablet computer, or a mobile phone.

Figure 2:
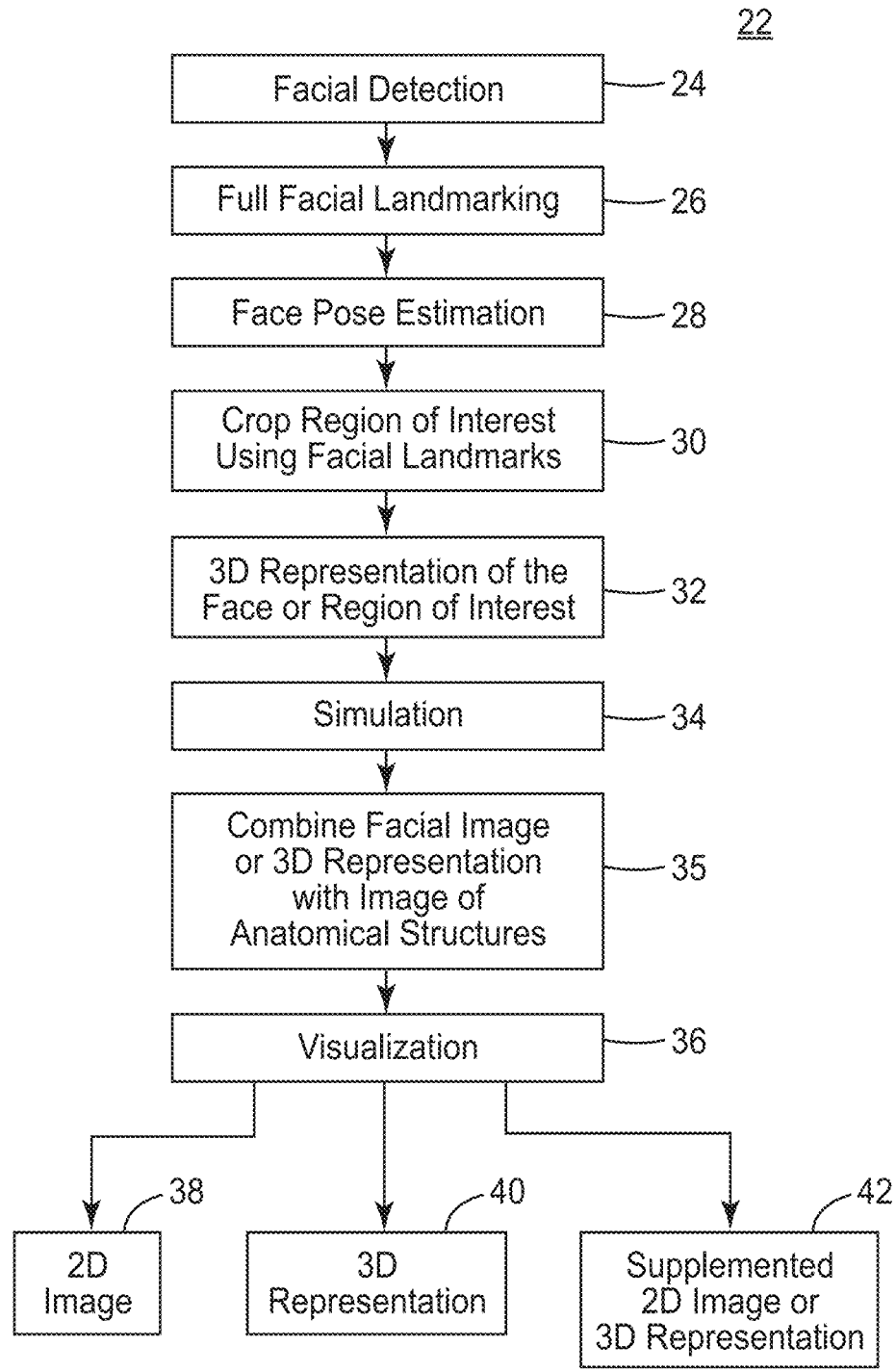
FIG. 2 is a flow chart of a method for simulating orthodontic treatment.

FIG. 2 is a flow chart of a method 22 for simulating orthodontic treatment. This method can be implemented in software or firmware modules for execution by a processor such as processor 16. This method is used to visualize a simulation of an orthodontic treatment through augmentation, a virtual overlay onto an image captured of the real world, possibly with manipulation of an estimated 3D representation of a face captured in one or more frames of video in real-time.

The following steps of method 22, more fully explained below, are used to produce an exemplary augmented orthodontic appliance simulation, starting with a single frame (image) of video: Facial Detection (step 24); Full Facial Landmarking (step 26); Face Pose Estimation (step 28); Crop Region of Interest Using Facial Landmarks (step 30); optional 3D Representation of the Face or region of interest (step 32); Simulation (step 34); optional supplementation of the image or 3D Representation of the Face (step 35); and Visualization (step 36).

Facial Detection (24)

Figure 3:
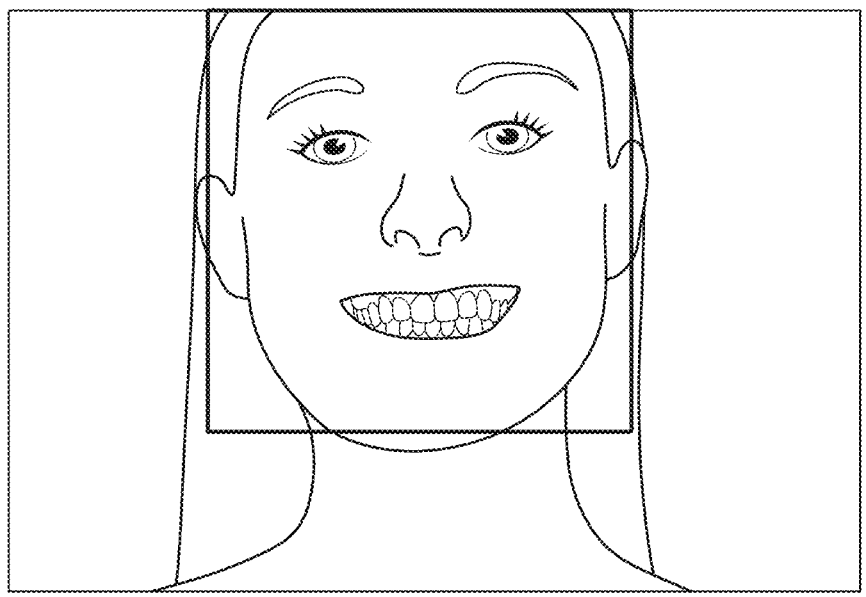
FIG. 3 is a representation of an image illustrating an example of a detected face.

This step finds a face in a frame of video from camera 12 using a pre-trained model, such as a Viola-Jones Model, an LBPH (Local Binary Pattern Histogram) cascade, or a model trained through deep learning. Once a face has been detected, a face context may be created to keep track of this face over multiple frames. This face context may contain previous frame data, such as important features used in reprojection, or a point cloud obtained over multiple previous frames. FIG. 3 is a representation of an image illustrating an example of a detected face as received from camera 12, where the box in the image indicates the area of detection. The image in FIG. 3 can optionally be an image of a user with orthodontic appliances in order to virtually remove the appliances rather than virtually adding appliances.

Full Facial Landmarking (26)

Figure 4:
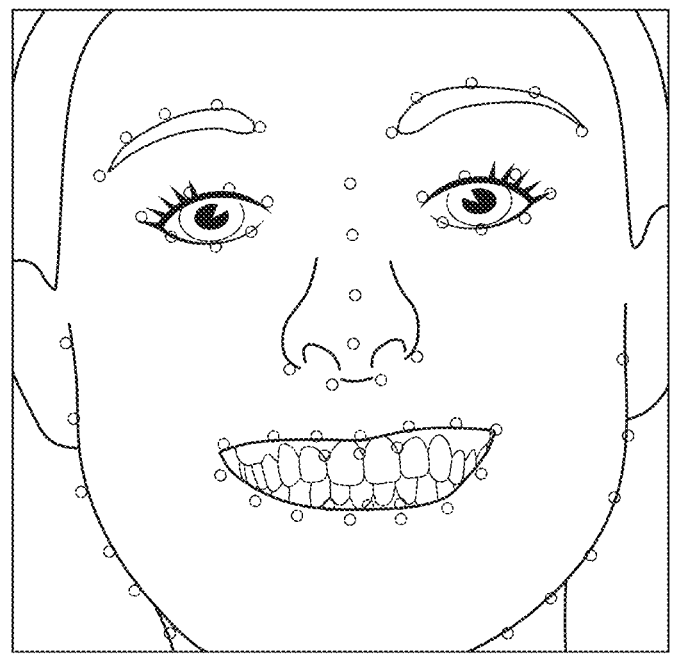
FIG. 4 is a representation of an image illustrating facial landmarking.

Landmarks are points of interest describing important structures on the face, and can be found using a shape predictor model which may use an SVM (Support Vector Machine), PCA (Principal Component Analysis), or deep learning and other machine learning algorithms like random forests. These landmarks are used to crop the face or region of interest from the background, and in this example, will be used for rough face pose estimation using a generalized 3D landmark model. They can also be used in the steps below to morph a generalized face mesh to more accurately represent the face detected in the video. FIG. 4 is a representation of an image illustrating facial landmarking, where the detected area from the image of FIG. 3 includes dots, or other indicia, for the landmarking.

Face Pose Estimation (28)

Using the detected facial landmarks and a generalized 3D landmark model, an estimated camera extrinsic model (transformation) can be found by solving the general Perspective N-Point (PNP) problem. Solving the PNP problem assumes the detected landmarks have not been affected by camera lens distortion (radial/tangential lens distortion), or have been undistorted. An SfM (Structure from Motion) technique could instead be applied on static (non-moving) parts of the face once the feature matching step below has been completed on multiple sequential frames to obtain a more accurate camera extrinsic model. Knowing the camera extrinsics provides a good 3D point representation of each of the landmarks which can help indicate the pose and further be used for more accurate augmented reality. This allows more accurate cropping of the region of interest for performing augmented reality, but it is not a required step. FIG. 5 is a representation of an image illustrating face pose estimation as indicated by the two boxes on the image from FIG. 3.

Crop Region of Interest Using Facial Landmarks (30)

This example will crop out the mouth region, where the inside edge of the lips represents the boundaries of the cropped region. This could be the full face or another part of the face if the simulation involves a large or different area of the face, such as the jaw. FIG. 6 illustrates a cropped region of interest from the images of FIGS. 3-5.

3D Representation of the Face or Region of Interest (32)

This is an optional step and only needed for simulations which require a 3D model of the face or region of the face, such as structural manipulation or improved accuracy for augmentation. Two methods could be used, or a combination of both.

Method 1. The first method that could be employed is to generate a 3D mesh over multiple frames of video, using Reprojection and Mesh reconstruction. Reprojection is the process of finding the depth of features in one of the images, turning the features into a 3D point cloud. Mesh reconstruction is the technique used to produce a triangle mesh from that point cloud. This assumes more than one image of the same face, where the images have been taken from slightly different angles and locations. The following are the steps of this Method 1.

i. Feature/Keypoint detection. These are points (corners) on an image that stand out among the rest of the pixels in the image, which are likely to be present in another image at a different angle of the same scene.

ii. Feature filtering. This is an optional step which may need to be taken if the list of features detected is too large. Various techniques exist to prune the list of features to get a smaller list of the strongest features (most prominent features).

iii. Feature correspondence. Each frame must have gone through the steps above, and have their own list of features. This is where the features from one image are matched with the features in the other image. Not all features will be matched, and any features which were not matched are discarded. Once the features have been matched, the list of features in the second image should be sorted in the same order as the features from the first image.

iv. Rectification. Adjust the features in each image so that they are row-aligned on the same plane using the camera extrinsic model. This means that features from one image are on the same x-axis row as the same feature in the other image.

v. Calculate the disparity map. The disparity map is a list of disparities (distances) on the x-axis between the matching points. The distances are measured in units of pixels.

vi. Triangulation. Using the geometric relation of the cameras, the method can calculate the epipolar geometry, and the essential and fundamental matrices needed to calculate the depth of each feature in one image.

vii. Mesh Reconstruction. Turn the 3D point cloud into a 3D mesh for the simulation step. This may also include finding texture coordinates through ray tracing based on camera parameters (e.g., camera location).

Method 2. This method involves a parametric representation of the face or region of interest (e.g., NURBS surface or Bézier surface), or a generic polygonal mesh (i.e., triangles or quadrilaterals), which will be morphed, expanded, or stretched to best fit either a point cloud of the face (see Method 1) or a set of landmarks obtained earlier. If using a generic mesh of a face or region of interest, vertices within the mesh could be assigned weights to landmarks. When the landmarks are found in the image, the vertices of the generic mesh would be pulled towards those landmarks based on their given weights and face pose.

Alternatively, the topology of the surface could be predefined only in the abstract, such as by graph-theoretical relationships between landmarks or regions outlined by lines between landmarks. As points are obtained in 3D via feature recognition (landmark identification) and photogrammetric triangulation, the NURBS surface or mesh could be generated such that the landmarks coincide with the corners of the surface patches. Of course, additional points may be necessarily captured in the regions between landmarks, and these points can serve to more accurately define the parameters of the surfaces: control points and polynomial coefficients in the case of NURBS or intermediate vertices in the case of tessellated mesh surfaces. Any distinct feature of the face can serve as a landmark or control point in a mesh or parametric model. As such, the accuracy of the model can be improved by increasing the resolution of the video imagery to the extent that these minute features are both visible and recognizable.

Simulation (34)

Once the steps above are complete, the virtual treatment can be applied, either through augmentation or manipulation of the 3D geometry. This may include pin-pointing locations or areas to apply the simulation. In this example, augmentation is implemented, where the rendered orthodontic appliance is overlaid onto the region of interest, after estimating the location on the region of interest where the appliance should be placed, or where detected appliances are virtually removed from the region of interest. For treatments involving manipulation of 3D geometry, extra steps may need to be taken, such as filling any holes in the image that result from morphing the 3D geometry. The rendered orthodontic appliance can be represented by a 2D image or a 3D model.

In this example, various image processing techniques are used on the region of interest to segment and identify the teeth, which include scaling-up the region of interest, noise reduction, applying a segmentation algorithm such as Mean Shift segmentation, histogram equalization, adaptive thresholding on specific channels of multiple color spaces, eroding and dilating (opening/closing), edge detection, and finding contours.

The region of interest is first scaled up and converted to different color spaces, where an adaptive threshold is applied to the channel in which the teeth are most separated from the non-teeth. FIGS. 7A-7C illustrate adaptive thresholding applied to inverted green-red channel of lab color space of region of interest: inverted channel "a" (green-red) of lab color space (FIG. 7A), mask after adaptive thresholding applied (FIG. 7B), and color image of region of interest with mask applied (FIG. 7C). FIGS. 8A-8C illustrate adaptive thresholding applied to luminance channel of YUV color space of region of interest: channel "Y" (luminance) of YUV color space (FIG. 8A), mask after adaptive thresholding applied combined (bitwise and) with mask from Lab color space adaptive threshold (FIG. 8B), and final color image of region of interest with combined mask applied (FIG. 8C).

Once a mask has been created through adaptive thresholding of the color space channels above, opening (eroding, then dilating) and closing (dilating, then eroding) can be used to further segment the teeth and clean up noise. FIGS. 9A and 9B illustrate, respectively, opening and closing of region of interest mask after color space thresholding.

Edges are detected from the mask, using a technique such as Canny Edge Detection. FIG. 10 illustrates detected edges from canny edge detection.

Contours can be generated from the detected edges, where individual teeth or groups of teeth can be analyzed or worked with as standalone objects. FIG. 11 illustrates closed contours found from detected edges, overlaid onto a color region of interest.

From the contour analysis, and general face pose, the treatment is rendered in the correct orientation and scale, ready to be overlaid on the region of interest. The original image could be analyzed to find a general lighting model to apply to rendered treatment, which would make the treatment augmentation fit more naturally in the scene. FIG. 12 illustrates virtual rendering of treatment, in this example brackets and archwires. Optionally, the virtual rendering can involve removing detected appliances such as brackets and archwires.

The rendered treatment is augmented onto the region of interest. Post processing can be done, such as Gaussian blur, to blend the augmented treatment with the original image and make the final image appear more natural, as if it were a part of the original image. FIG. 13 illustrates augmentation of treatment, where the virtual brackets and archwires are overlaid on the teeth within the region of interest. Optionally, the augmentation can involve removing detected appliances and displaying the result. Augmentation can be achieved without explicitly segmenting out individual teeth and contours but by doing direct registration of end points of the mouth with end points of teeth. However, identifying each tooth center even approximately provides a more accurate/realistic result.

Supplemented Images or 3D Models (35)

Another approach to augmenting images of the face with appliances, restorations, or modified anatomies involves another aspect of 3D modeling. The approach described above uses 3D modeling to determine the position, orientation, and scale of the face, which may be mathematically described by a 3D Affine transform in a virtual universe. A corresponding transform is then applied to the dental appliances so that they register to the teeth of the patient in somewhat realistic positions and orientations, although 2D image analysis may ultimately be used to find the Facial Axis (FA) points of the teeth at which to place brackets.

In this other approach, the video camera may be used as a type of 3D scanner, thereby capturing multiple 2D images of a person's face from different vantage points (i.e., viewpoints and look-at vectors, which together with the image plane form a set of distinct view frustums). Using 3D photogrammetry techniques, a 3D model of the person's face (and head) may be generated, originally in the form of a point cloud, then later in the form of a triangular mesh. Accompanying these techniques is UV mapping (or texture mapping) to apply color values from pixels in the 2D images to 3D vertices or triangles in the mesh. As such, a realistic-looking and reasonably accurate 3D model of the person's face may be generated in the virtual universe. Subsequently, an image of the 3D model may be rendered onto a 2D plane that is positioned anywhere in the virtual universe according to a view frustum. Suitable rendering methods include polygon rendering or ray tracing. The color values from the UV map would be applied in the rendering to generate a more realistic, color rendition of the face (as opposed to a monochromatic mesh model shaded only by triangle orientation relative to both the view point and each light source in the scene).

At this point, the 3D model of the face can be combined or integrated (or simply registered) with other 3D models or images that were optionally obtained from different scan sources, such as intraoral scanners, Cone Beam CT (CBCT or 3D X-ray) scanners, MRI scanners, 3D stereoscopic cameras, and the like. Such data would likely have been obtained at earlier dates and used in treatment planning. Such other models or images can be stored in and retrieved from, for example, data storage 19.

In some cases, the video imagery may serve as the sole source of superficial 3D imagery, thus capturing the soft tissues of the face and whatever dental anatomy may be visible. In other cases, soft tissue data may be captured in CBCT scans (without color information) or in 3D stereoscopic imagery. Regardless, soft tissue data is an essential component in the modeling of certain treatment plans, such as those involving orthognathic surgery, occlusion class correction (via antero-posterior dental movements), significant changes to the anterior proclination of teeth, and cosmetic and plastic surgeries. Embodiments of this invention can thus provide visual feedback to patients on their expected outward appearance resulting from treatment, during or after the treatment, or both during and after.

By capturing multiple 3D data sources of the patient's craniofacial anatomy, a doctor may be able to conscientiously devise one or more treatment plans with a real basis in structural anatomy. These plans may be devised on the doctor's own schedule, without the patient present, and possibly in collaboration with other doctors, technicians, or service providers. Appliances or prostheses may be created and applied to the patient's natural anatomy, and the patient's naturally anatomy can be augmented or modified as part of the treatment plan. 3D virtual models of such appliances and prostheses can be created by, for example, third party labs or service providers and combined with the datasets provided by the doctor. Modified anatomies resulting from treatment can be generated by the doctor, by a third party, or as a collaborative effort using remote software collaboration tools. The treatment plan can be presented back to the patient for review, possible modification, and approval. In some scenarios, the doctor may be the reviewer, and a third party lab or manufacturer is the source of the proposed treatment plan.

In presenting the treatment plan back to the patient, a video camera is used to capture enough frames to generate a 3D model of the patient sufficient to register his/her face to the 3D model comprising the plan, which may be based on other data sources but having at least some anatomical features in common with the newly-captured data. A complete re-scan of the patient's face would not be necessary, since a full scan would have already been done at an earlier date in order to facilitate the creation of a detailed treatment plan. Thus, with only limited motion relative to the video camera, a partial 3D model of the patient's current anatomy could be created, optionally cropped to remove the portions of anatomy modified by the plan, and best-fit to the plan model. Because the view frustum of each video frame is known via 3D photogrammetry methods, the same view frustum may be used to represent a virtual camera, and a 2D rendering of the 3D model may be created on the view plane of this camera. This 2D rendering can then be presented back to the patient (or other observer) in real-time as the patient moves relative to the camera. In effect, the physical and virtual worlds are kept synchronous with one another.

There are options in determining what to render and present back to the patient. For example, it might not be necessary to store a texture map in the plan model if the plan is only presented in real-time with the patient present. In this scenario, the registration between individual video frames and the plan model can occur without the use of a texture map, and the color value of each pixel in the video image presented back to the patient can simply pass-through from the value captured by the video camera. In the case of appliances being attached to the patient's teeth (or other parts of the face), the appliances would be rendered in the virtual world, and their 2D renditions would overlay corresponding areas from the video frames, in effect masking the underlying anatomy. In the case of modified anatomies, the same method could be used, except the pixels of these anatomies may need to be colored using previously captured values that were UV mapped onto the mesh of the plan model. Alternatively, the color values could be obtained from the current video frame but then transformed to different positions as determined by morphs to the 3D anatomy according to the treatment plan. For example, an orthognathic surgery might prescribe that the mandible be advanced by several millimeters. The color values of the pixels used to render the patient's soft tissues (skin and lips) affected by the advancement would need not to differ as a result; only their positions in the virtual world and thus the rendering would change. As such, the affected pixels in the 2D video image might simply by translated in the image plane according to a 3D Affine transform projected onto the view plane. In yet other scenarios, once the registration of the physical video camera is established with the virtual camera, the entire 3D virtual scene may be rendered in real-time and presented back to the patient in sync with their head movements.

In some of the above scenarios, a technique can be employed by which the plan model is continuously augmented or updated while video is being captured for the purpose of presenting the treatment plan to the patient. Given that in some scenarios only minimal video coverage might have been used to generate a 3D model of the patient, holes, islands, or noisy regions are likely to exist in the mesh comprising the model. As new video images are received, even if the main purpose of capture is to register physical and virtual worlds and render an existing plan model for the patient, the new images can be used to augment or update the existing model by filling holes, removing or joining islands, and reducing noise. In so doing, the quality of the plan model may be improved in real-time (or after a brief processing delay). In some instances, the dimensional accuracy of the model may be improved by using large, unitary patches of scan data to adjust the positions and orientations of smaller patches that were stitched together with accumulated error. This technique could also be used to improve the realism of an avatar-style rendering by updating the texture map to current skin and lighting conditions. Otherwise, the texture map used on the avatar would have come from a previous scan captured at an earlier date and possibly in a different setting.

For the supplemented image or model, the user's facial image or 3D representation can optionally be registered with the image or model of the user's facial anatomy using, for example, PCA or other techniques. When registered, the images or models are synchronized such that manipulation of one image or representation causes corresponding manipulation of the other image or representation. For example, if the user's facial image is rotated, the registered image or model of the user's facial anatomy is correspondingly rotated.

Visualization (36)

Figures 14A, 14B, 14C, 14D:
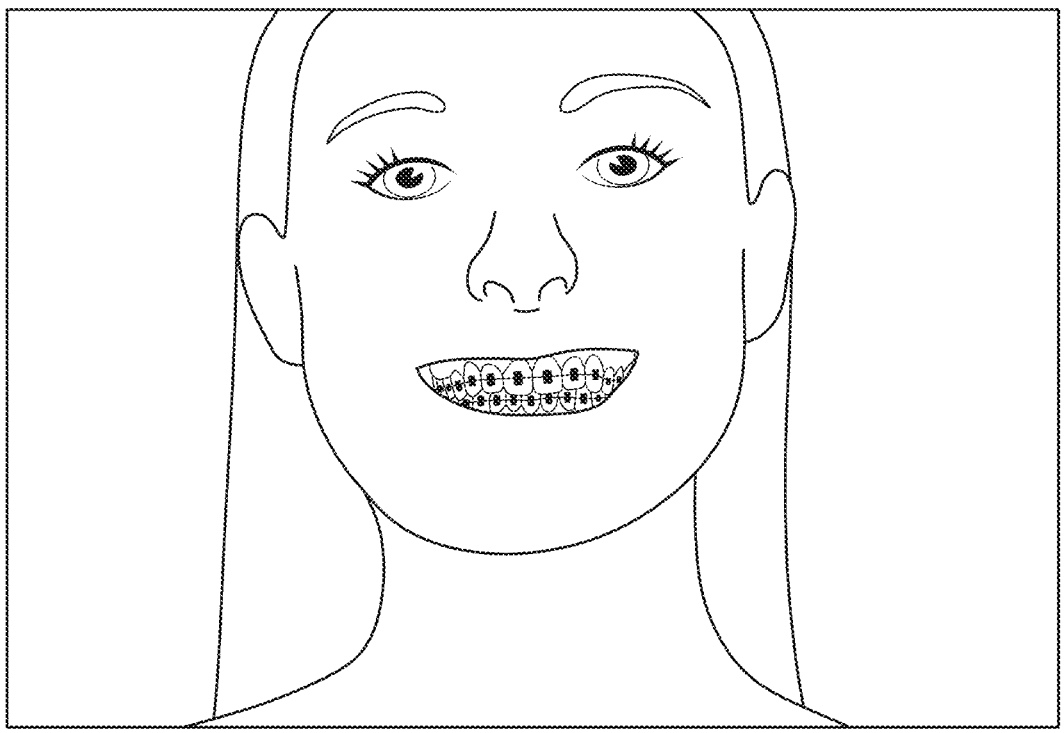
FIG. 14A is a user interface illustrating treatment augmentation in a representation of a single image.
FIG. 14B is a user interface representing a 3D model augmented with 3D appliances.
FIG. 14C is a user interface representing a 2D image augmented with appliances and anatomical structures.
FIG. 14D is a user interface representing a 3D model augmented with 3D appliances and anatomical structures.

This step involves overlaying the region of interest onto the original frame (FIG. 3) and displaying the final image to the user for a 2D image (38). FIG. 14A illustrates the result of treatment augmentation in a representation of a single image displayed to the user via display device 14 and within a user interface, for example. Optionally, the single image of FIG. 14A can display the result of virtually removing detected appliances worn by the user.

If a 3D representation of the user's face is generated, using the optional step 32, then such 3D representation can be displayed augmented with the virtual treatment (40) as represented by the user interface in FIG. 14B for display on display device 14. If a supplemented 2D image or a 3D representation is generated, using the optional step 35, then such supplemented 2D image or 3D representation can be displayed augmented with the virtual treatment (42) as represented by the user interfaces in FIGS. 14C and 14D for display on display device 14.

Method 22 can be executed by processor 16 such that the augmentation is shown to the user on display device 14 in real-time when or shortly after detection of the user's image by camera 12. The term "real-time" means at a rate of at least one frame per second or, more preferably, at a rate of 15-60 frames per second.

The invention claimed is:

1. A method for simulating orthodontic treatment, the method comprising:
receiving an electronic image;
detecting, using a trained deep learning model, a facial image within the electronic image;
landmarking the facial image using a trained machine learning model;
estimating a face pose associated with the electronic facial image based on the landmarking;
identifying, based on the landmarking and estimated face pose, a region of interest in the facial image, such that the region of interest includes a representation of one or more teeth;
virtually overlaying images representing orthodontic appliances on the region of interest to form a treatment-simulated image; and
outputting, for display, the treatment-simulated image via an electronic display device.

2. The method of claim 1, wherein receiving the electronic image comprises detecting the electronic image from one or more video frames.

3. The method of claim 1, wherein virtually overlaying the images representing the orthodontic appliances on the region of interest to form the treatment-simulated image comprises virtually overlaying respective images representing brackets and an archwire on the region of interest to form the treatment-simulated image.

4. The method of claim 1, wherein the treatment-simulated image comprises a three-dimensional electronic representation of the facial image overlaid with the virtual orthodontic appliances.

5. The method of claim 1, wherein virtually overlaying the images representing the orthodontic appliances on the region of interest to form the treatment-simulated image comprises:
    extracting the region of interest from the electronic facial image;
    augmenting the extracted region of interest using the images representing the orthodontic appliances to form an augmented region of interest; and
    superimposing the augmented region of interest on the electronic facial image to form the treatment-simulated image.

6. A system for simulating orthodontic treatment, the system comprising:
    camera hardware configured to capture digital image data;
    an electronic display device; and
    one or more processors electronically coupled to the camera and the electronic display device, the one or more processors being configured to:
        receive the digital image data from the camera hardware;
        obtain, from the received digital image data, an electronic image;
        detect, using a trained deep learning model, a facial image within the electronic image;
        landmark the facial image using a trained machine learning model;
        estimate a face pose associated with the facial image based on the landmarking;
        identify, based on the landmarking and the estimated face pose, a region of interest in the facial image, such that the region of interest including a representation of one or more teeth;
        virtually overlay images representing orthodontic appliances on the region of interest to form a treatment-simulated image; and
        output, for display via the electronic display device, the treatment-simulated image.

7. The system of claim 6, wherein the digital image data comprises video data, and wherein to obtain the facial image, the one or more processors are configured to detect the electronic image in a frame of the video data received from the camera hardware.

8. The system of claim 6, wherein to virtually overlay the images representing the orthodontic appliances on the region of interest to form the treatment-simulated image, the one or more processors are configured to virtually overlay respective images representing brackets and an archwire on the region of interest to form the treatment-simulated image.

9. The system of claim 6, wherein the one or more processors are further configured to generate treatment-simulated image comprises a three-dimensional electronic representation of the facial image overlaid with the virtual orthodontic appliances.

10. The system of claim 6, wherein the one or more processors are configured to receive the digital image data, obtain the electronic facial image, identify the region of interest, virtually overlay the images representing the orthodontic appliances, and output the treatment-simulated image for display at a rate of at least one frame per second.

11. The system of claim 10, wherein the rate of at least one frame per second is a rate of fifteen to sixty frames per second.

12. A method for simulating a result of orthodontic treatment, the method comprising:
    receiving an electronic image;
    detecting, using a trained deep learning model, a facial image within the electronic image;
    landmarking the facial image using a trained machine learning model;
    estimating a face pose associated with the facial image based on the landmarking;
    identifying, based on the landmarking and the estimated face pose, a region of interest in the facial image such that the region of interest includes representations of one or more teeth and orthodontic appliances placed on the teeth;
    removing the representations of the orthodontic appliances from the facial image to form a simulated post-treatment image; and
    outputting, for display, the simulated post-treatment image via an electronic display device.

13. A method for simulating orthodontic treatment, the method comprising:
    receiving an electronic facial image;
    receiving an electronic image or model of a facial anatomy corresponding to the electronic facial image;
    detecting, using a trained deep learning model, a facial image within the electronic image;
    landmarking the facial image using a trained machine learning model;
    estimating a face pose associated with the electronic facial image based on the landmarking;
    identifying, based on the landmarking and the estimated face pose, a region of interest in the facial image such that the region of interest includes a representation of one or more teeth;
    virtually overlaying images representing orthodontic appliances on the region of interest to form a treatment-simulated image; and
    outputting, for display via an electronic display device, the treatment-simulated image with the electronic image or model of the corresponding facial anatomy.

14. The method of claim 13, wherein the electronic image or model of the corresponding facial anatomy comprises an X-ray image.

15. The method of claim 13, wherein the electronic image or model of the corresponding facial anatomy comprises a cone beam computed tomography (CBCT) image.

16. The method of claim 13, wherein the treatment-simulated image comprises a three-dimensional electronic representation of the electronic facial image overlaid with the virtual orthodontic appliances and with the electronic image or model of the corresponding facial anatomy.

* * * * *